United States Patent
Park et al.

(10) Patent No.: US 10,287,373 B2
(45) Date of Patent: May 14, 2019

(54) LIGAND COMPOUND, CATALYST SYSTEM FOR OLEFIN OLIGOMERIZATION, AND METHOD FOR OLIGOMERIZING OLEFINS USING THE SAME

(71) Applicant: LG Chem, Ltd., Seoul (KR)

(72) Inventors: Jin Young Park, Daejeon (KR); Yong Ho Lee, Daejeon (KR); Eun Ji Shin, Daejeon (KR); Seok Pil Sa, Daejeon (KR); Ki Soo Lee, Daejeon (KR); Seul Ki Im, Daejeon (KR); Yoon Ki Hong, Daejeon (KR)

(73) Assignee: LG Chem, Ltd. (KR)

(*) Notice: Subject to any disclaimer, the term of this patent is extended or adjusted under 35 U.S.C. 154(b) by 34 days.

(21) Appl. No.: 15/527,898

(22) PCT Filed: Oct. 21, 2016

(86) PCT No.: PCT/KR2016/011919
§ 371 (c)(1),
(2) Date: May 18, 2017

(87) PCT Pub. No.: WO2017/069575
PCT Pub. Date: Apr. 27, 2017

(65) Prior Publication Data
US 2018/0327528 A1 Nov. 15, 2018

(30) Foreign Application Priority Data

Oct. 21, 2015 (KR) .................. 10-2015-0146843
Feb. 5, 2016 (KR) .................. 10-2016-0015301

(51) Int. Cl.
*C07C 2/32* (2006.01)
*C07C 2/08* (2006.01)
*C07F 9/28* (2006.01)
*B01J 31/32* (2006.01)
*C08F 210/14* (2006.01)
*C07F 9/02* (2006.01)
*C07F 9/24* (2006.01)
*C08F 4/69* (2006.01)
*C08F 10/00* (2006.01)
*B01J 31/12* (2006.01)
*C07F 9/50* (2006.01)
*C07F 9/70* (2006.01)
*C07F 9/90* (2006.01)
*C07C 11/107* (2006.01)
*C08F 4/42* (2006.01)
*C07F 9/46* (2006.01)

(52) U.S. Cl.
CPC .............. *C08F 210/14* (2013.01); *B01J 31/12* (2013.01); *B01J 31/32* (2013.01); *C07C 2/08* (2013.01); *C07C 2/32* (2013.01); *C07C 11/107* (2013.01); *C07F 9/02* (2013.01); *C07F 9/24* (2013.01); *C07F 9/28* (2013.01); *C07F 9/46* (2013.01); *C07F 9/50* (2013.01); *C07F 9/70* (2013.01); *C07F 9/90* (2013.01); *C08F 4/42* (2013.01); *C08F 4/69* (2013.01); *C08F 10/00* (2013.01)

(58) Field of Classification Search
CPC ...... C07C 2/32; C07C 2/08; C07F 9/28; B01J 31/22
See application file for complete search history.

(56) References Cited

U.S. PATENT DOCUMENTS

| | | |
|---|---|---|
| 8,334,420 B2 | 12/2012 | Small et al. |
| 2006/0020091 A1 | 1/2006 | Blann et al. |
| 2010/0081777 A1 | 4/2010 | Gao et al. |
| 2012/0172645 A1 | 7/2012 | Sydora |
| 2015/0111858 A1 | 4/2015 | Tanol et al. |
| 2015/0132807 A1 | 5/2015 | Agard et al. |
| 2015/0178475 A1 | 6/2015 | Sydora et al. |
| 2016/0045906 A1 | 2/2016 | Sa et al. |
| 2016/0122371 A1 | 5/2016 | Lee et al. |
| 2016/0207946 A1 | 7/2016 | Shin et al. |
| 2017/0029346 A1 | 2/2017 | Lee et al. |

FOREIGN PATENT DOCUMENTS

| | | |
|---|---|---|
| CN | 1398835 A | 2/2003 |
| CN | 102040624 B | 6/2014 |
| CN | 104511311 A | 4/2015 |
| EP | 0681217 A1 | 11/1995 |
| EP | 0705839 A1 | 4/1996 |
| EP | 1241522 A1 | 9/2002 |
| KR | 20090017929 A | 2/2009 |
| KR | 20130142151 A | 12/2013 |
| KR | 20150006474 A | 1/2015 |
| KR | 20150058048 A | 5/2015 |

(Continued)

OTHER PUBLICATIONS

Carter A. et al., "High Activity Ethylene Trimerisation Catalysts Based on Diphosphine Ligands", Chem. Commun., Mar. 2002, pp. 858-859.
Du Toit, A. et al., "Styrene-ethylene Co-oligomerization with Bis-(Diphenylphosphino)—Amine/Chromium Catalysts and the Use of the Co-oligomerization Products in Copolymerization Reactions with Metallocenes", Journal of Polymer Science Part A: Polymer Chemistry, Feb. 2008, vol. 46, No. 4, pp. 1488-1501.

(Continued)

Primary Examiner — Caixia Lu
(74) Attorney, Agent, or Firm — Lerner, David, Littenberg, Krumholz & Mentlik, LLP

(57) ABSTRACT

The present invention relates to a ligand compound, a catalyst system for olefin oligomerization, and a method for oligomerizing olefins using the same. The ligand compound according to the present invention has a structure in which a substituent is substituted in the trans form, and thereby when used for olefin oligomerization, the activity of the catalyst used and the selectivity of 1-hexene and 1-octene can be increased.

10 Claims, No Drawings

(56) References Cited

FOREIGN PATENT DOCUMENTS

| | | |
|---|---|---|
| KR | 20150058049 A | 5/2015 |
| KR | 20160099462 A | 8/2016 |
| WO | 2001072271 A2 | 10/2001 |
| WO | 2001072272 A2 | 10/2001 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2005123633 A1 | 12/2005 |
| WO | 2006108803 A1 | 10/2006 |
| WO | 2007007272 A2 | 1/2007 |
| WO | 2007057455 A1 | 5/2007 |
| WO | 2007057458 A1 | 5/2007 |
| WO | 2008014139 A2 | 1/2008 |
| WO | 2013068437 A2 | 5/2013 |
| WO | 2015083053 A1 | 6/2015 |

OTHER PUBLICATIONS

International Search Report for PCT/KR2016/011645 dated Feb. 9, 2017.

International Search Report for PCT/KR2016/011919 dated Feb. 9, 2017.

Jiang, T. et al., "The Effect of N-aryl Bisphospbineamine Ligands on the Selective Ethylene Tetramerization", Journal of Molecular Catalysis A: Chemical, Jan. 2008, vol. 279, No. 1, pp. 90-93.

Killian, E. et al., "The Use of Bis (Diphenylphosphino) Amines with N-aryl Functionalities in Selective Ethylene Tri- and Tetramerisation", Journal of Molecular Catalysis A: Chemical, Jun. 2007, vol. 270, Nos. 1-2, pp. 214-218.

Kuhlmann, S. et al., "N-substituted Diphosphinoamines: Toward Rational Ligand Design for the Efficient Tetramerization of Ethylene", Journal of Catalysis, Jan. 2007, vol. 245, No. 2, pp. 279-284.

LIGAND COMPOUND, CATALYST SYSTEM FOR OLEFIN OLIGOMERIZATION, AND METHOD FOR OLIGOMERIZING OLEFINS USING THE SAME

CROSS-REFERENCE TO RELATED APPLICATION(S)

The present application is a national phase entry under 35 U.S.C. § 371 of International Application No. PCT/KR2016/011919, filed Oct. 21, 2016, published in Korean, which claims priority from Korean Patent Application No. 10-2015-0146843 filed on Oct. 21, 2015 and Korean Patent Application No. 10-2016-0015301 filed on Feb. 5, 2016, all of which are incorporated herein by reference.

TECHNICAL FIELD

The present invention relates to a ligand compound, a catalyst system for olefin oligomerization, and a method for oligomerizing olefins using the same.

BACKGROUND OF ART

Linear alpha-olefins are widely used commercially as important materials used for comonomers, detergents, lubricants, plasticizers, etc., and in particular, 1-hexene and 1-octene are widely used as comonomers for controlling the density of polyethylene during the preparation of linear low-density polyethylene (LLDPE).

In existing preparation processes of linear low-density polyethylene (LLDPE), ethylene is copolymerized with alpha-olefins, for example, comonomers such as 1-hexene and 1-octene, so to control the density thereof by forming branches in a polymer backbone.

Accordingly, for the preparation of LLDPPE with a high content of copolymers, there was a problem in that the cost of comonomers occupies a large part of preparation costs. There have been various attempts to solve these problems.

In addition, since alpha-olefins have various different application fields or market sizes according to the kind, a technology of selectively producing a specific olefin is commercially very important, and recently, many studies are being progressed on the chromium catalyst technology for preparing 1-hexene or 1-octene with high selectivity through selective ethylene oligomerization.

Existing commercial preparation methods for preparing 1-hexene or 1-octene include the SHOP process of Shell Chemical, the Ziegler process of Chevron Philips, and the like, whereby C4-C20 alpha-olefins with a wide distribution can be produced.

As a catalyst for trimerization of ethylene, a chromium-based catalyst using a ligand of the general formula (R1)(R2)X-Y-X(R3)(R4) has been proposed. In the formula above, X is phosphorus, arsenic, or antimony, Y is a linking group such as —N(R5)-, and at least one of R1, R2, R3, and R4 has a polar or electron-donating substituent.

Additionally, as a ligand that exhibits catalytic activity to 1-hexene under catalytic conditions, studies have been progressed on o-ethylphenyl)$_2$PN(Me)P(o-ethylphenyl)$_2$, which does not have a polar substituent on at least one of R1, R2, R3 and R4 (*Chem. Commun.*, 2002, 858).

However, with regard to ligands containing heteroatoms of the above-mentioned prior art, there has been a continuing demand for multimerization reaction activity and high selectivity which are consistently maintained during the reaction when preparing 1-octene or 1-hexene.

In view of the above, the inventors of the present invention conducted intensive studies on ligands capable of solving the above-mentioned problems, and as a result, found that a trans type ligand is suitable for olefin oligomerization as described later, thereby completing the present invention.

DETAILED DESCRIPTION OF THE INVENTION

Technical Problem

It is an object of the present invention to provide a novel ligand compound that can oligomerize olefins with high catalytic activity and selectivity, a catalyst system for olefin oligomerization including the same, and a method for oligomerizing olefins using the same.

Technical Solution

In order to achieve the objects, the present invention provides a compound represented by Chemical Formula 1 or 2 below:

[Chemical Formula 1]

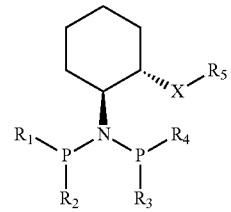

[Chemical Formula 2]

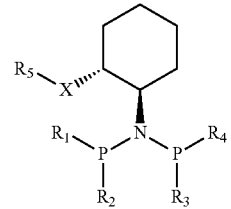

in Chemical Formula 1 and 2, $R_1$ to $R_4$ are each independently $C_{1-10}$ alkyl; $C_{3-6}$ cycloalkyl unsubstituted or substituted by $C_{1-10}$ alkyl or $C_{1-10}$ alkoxy; $C_{6-20}$ aryl unsubstituted or substituted by $C_{1-10}$ alkyl or $C_{1-10}$ alkoxy; or $C_{5-20}$ heteroaryl unsubstituted or substituted by $C_{1-10}$ alkyl or $C_{1-10}$ alkoxy, $R_5$ is $C_{1-10}$ alkyl; $C_{3-6}$ cycloalkyl unsubstituted or substituted by $C_{1-10}$ alkyl or $C_{1-10}$ alkoxy; $C_{6-20}$ aryl unsubstituted or substituted by $C_{1-10}$ alkyl or $C_{1-10}$ alkoxy; or $C_{5-20}$ heteroaryl unsubstituted or substituted by $C_{1-10}$ alkyl or $C_{1-10}$ alkoxy, and X is a bond or $C_{1-5}$ alkylene.

The present invention relates to a ligand compound constituting a catalyst system for olefin oligomerization together with a source of transitional metal and a cocatalyst. The compound represented by Chemical Formula 1 or 2 is a P—N—P type ligand compound, and phosphorus and nitrogen are substituted with a specific substituent to give a steric bulk, thereby enabling selective olefin oligomerization.

As used herein, the term "olefin oligomerization" means polymerization of a small number of olefins. Depending on the number of olefins to be polymerized, it is referred to as trimerization or tetramerization, and is collectively referred to as multimerization. In particular, in the present invention, it refers to selectively preparing 1-hexene and 1-octene, which are the main comonomers of LLDPE, from ethylene.

Such a selective olefin oligomerization reaction is closely related to a catalyst system used. A catalyst system used in olefin oligomerization reactions comprises a source of transition metal functioning as a main catalyst, and a cocatalyst, wherein the structure of an active catalyst can be modified according to the chemical structure of a ligand, thereby varying olefin selectivity.

In particular, in the present invention, the compound represented by Chemical Formula 1 or 2 is characterized in that a substituent of —N(PR$_1$R$_2$)(PR$_3$R$_4$) and a substituent of —X—R$_5$ are substituted in the trans form.

Without being bound by any theory, cis-type and trans-type exhibit different reactivity during oligomerization reaction, respectively, which is attributed to the difference in coordination form with a transition metal depending on the structure of the ligand. Therefore, the present invention uses a trans-type ligand for olefin oligomerization, thereby enhancing the oligomerization activity and increasing the selectivity of 1-hexene and 1-octene.

In Chemical Formula 1 or 2, R$_1$ to R$_4$ are preferably identical to one another. Further, preferably, R$_1$ to R$_4$ are all phenyl.

In Chemical Formula 1 or 2, —X—R$_5$ can be prepared in the trans form due to steric hindrance with —N(PR$_1$R$_2$)(PR$_3$R$_4$). Thus, as the size thereof is larger, the production of trans-type is facilitated.

Preferably, R$_5$ is ethyl, propyl, isopropyl, butyl, isobutyl, sec-butyl, pentyl, isopentyl, neopentyl, tert-pentyl, sec-pentyl, 3-pentyl, cyclopropyl, cyclobutyl, cyclopentyl, cyclohexyl, cyclohexyl substituted with methyl, or phenyl. Further, preferably, X is a bond or methylene (—CH$_2$—).

Further, preferably, R$_5$ is C$_{3-5}$ cycloalkyl, or C$_{6-20}$ aryl, and X is methylene. Further, preferably, R$_5$ is C$_{1-10}$ alkyl, or C$_{3-6}$ cycloalkyl, and X is a bond.

Representative examples of the compound represented by Chemical Formula 1 or 2 are as follows:

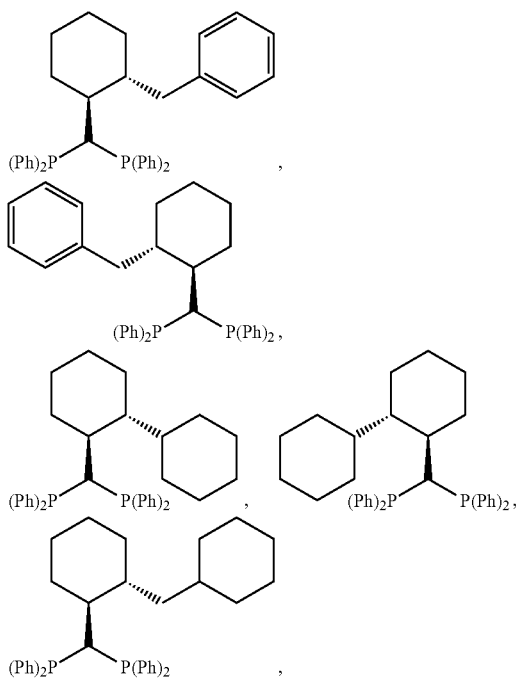

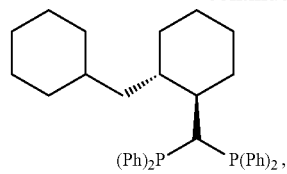

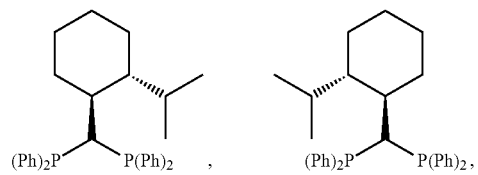

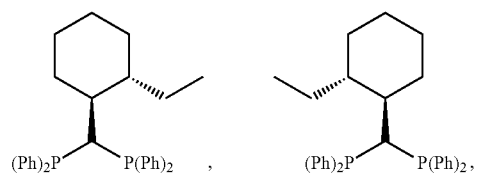

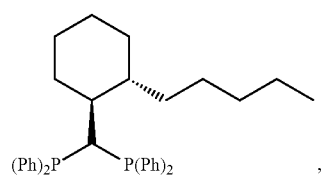

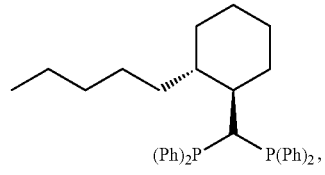

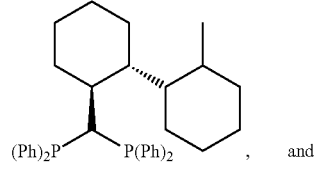
, and

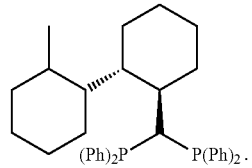
.

The present invention also provides a process for preparing the compound represented by Chemical Formula 1 or 2, as shown in Reaction Scheme 1 below:

[Reaction Scheme 1]

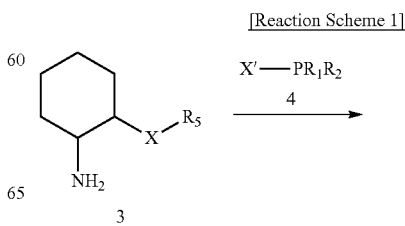

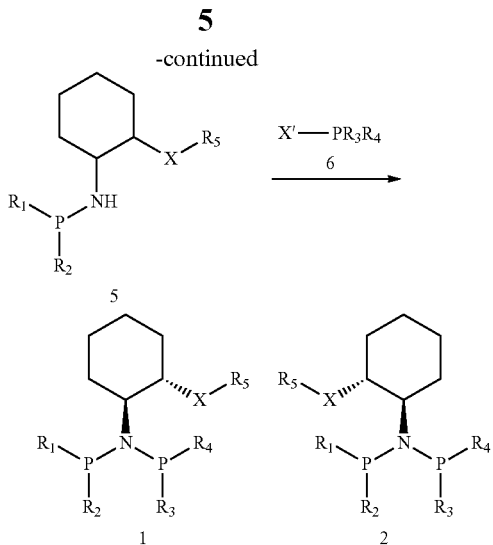

In Reaction Scheme 1, the definitions of X and $R_1$ to $R_5$ are the same as defined above, and each of X' represents a substituent which is eliminated upon reaction with an amine of the starting material. Examples of the substituent to be eliminated may include halogen, preferably chloro.

In the reaction scheme 1, the order of the first step and the second step may be changed, and if X—$PR_1R_2$ and X—$PR_3R_4$ are identical, the second step may be omitted. As the solvent for the reaction, dichloromethane is preferable, and the reaction is carried out preferably in the presence of triethylamine.

According to the first reaction, an amine group of the compound represented by Chemical Formula 3, which is the starting material, reacts with a compound represented by Chemical Formula 4 to prepare a compound represented by Chemical Formula 5.

Then, by the second reaction, a compound represented by Chemical Formula 1 or 2 can be produced by reacting the amine group of the compound represented by Chemical Formula 5 with the compound represented by Chemical Formula 6. At this time, due to the steric hindrance by the substituent of —X—$R_5$ of the compound represented by Chemical Formula 5, a trans-type compound like the compound represented by Chemical Formula 1 or 2 is produced, and a cis-type compound is not substantially produced.

Further, since the unreacted materials (the compounds represented by Chemical Formulas 3, 4 and 6), the intermediate (the compound represented by Chemical Formula 5) and other salt compounds remain in the final product, a step of eliminating these compounds from the product may be further included. The above elimination can be carried out by a method commonly used in the art. For example, in order to eliminate the salt compound, it is possible to use a method in which a polar solvent (for example, THF) is first added to perform separation and elimination, and then a solvent (for example, acetonitrile) capable of dissolving the remaining substances other than the compounds represented by Chemical Formulas 1 and 2 is added to perform separation and elimination.

In addition, the present invention provides a catalyst system for olefin oligomerization, comprising a compound represented by Chemical Formula 1 or 2, a source of transition metal and a cocatalyst.

As described above, when the compound represented by Chemical Formula 1 or 2 according to the present invention is used as a ligand, the activity of the catalyst and the selectivity of 1-hexene and 1-octene can be increased. Further, the catalyst system for olefin oligomerization may include both the compound represented by Chemical Formula 1 and the compound represented by Chemical Formula 2. Moreover, the catalyst system for olefin oligomerization may include two or more compounds represented by Chemical Formula 1 or 2 described above.

The source of transition metal of the catalyst system for olefin oligomerization of one embodiment described above functions as a main catalyst and may preferably be at least one selected from the group consisting of chromium(III) acetylacetonate, chromium trichloride tris-tetrahydrofuran, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate, and chromium(III)acetate hydroxide.

Further, the cocatalyst is an organometallic compound comprising a Group 13 metal, and is not particularly limited, as long as it can be generally used when multimerizing olefins in the presence of a catalyst of a transition metal compound. Specifically, as the cocatalyst, at least one selected from the group consisting of compounds represented by Chemical Formulas 3 to 5 below can be used:

$$-[Al(R_6)-O]_c- \quad \text{[Chemical Formula 3]}$$

in Chemical Formula 3,
$R_6$ is each independently halogen, $C_{1-20}$ alkyl, or $C_{1-20}$ haloalkyl, and
c is an integer of 2 or greater, $$D(R_7)_3 \quad \text{[Chemical Formula 4]}$$

in Chemical Formula 4,
D is aluminum or boron, and
$R_7$ is each independently hydrogen, halogen, $C_{1-20}$ hydrocarbyl, or $C_{1-20}$ hydrocarbyl substituted with halogen, $$[L-H]^+[Q(E)_4]^- \quad \text{[Chemical Formula 5]}$$

in Chemical Formula 5,
L is a neutral Lewis base,
$[L-H]^+$ is a Braønsted acid,
Q is $B^{3+}$ or $Al^{3-}$, and
E is each independently $C_{6-20}$ aryl or $C_{1-20}$ alkyl, wherein the $C_{6-20}$ aryl or $C_{1-20}$ alkyl is unsubstituted or substituted with at least one substituent selected from the group consisting of halogen, $C_{1-20}$ alkyl, $C_{1-20}$ alkoxy, and phenoxy.

The compound represented by Chemical Formula 3 may be, for example, modified methyl aluminoxane (MMAO), methyl aluminoxane (MAO), ethyl aluminoxane, isobutyl aluminoxane, butyl aluminoxane, etc.

The alkyl metal compound represented by Chemical Formula 4 may be, for example, trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminum methoxide, dimethylaluminum ethoxide, trimethylboron, triethylboron, triisobutylboron, tripropylboron, tributylboron, etc.

The compound represented by Chemical Formula 5 may be, for example, triethylammonium tetraphenylboron, tributylammonium tetraphenylboron, trimethylammonium tetraphenylboron, tripropylammonium tetraphenylboron, trimethylammonium tetra(p-tolyl)boron, tripropylammonium tetra(p-tolyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylboron, triphenylcarbonium tetraphenylaluminum, triphenylcarbonium tetra(p-trifluoromethylphenyl)boron, triphenylcarbonium tetrapentafluorophenylboron, etc.

As the cocatalyst of the catalyst system for olefin oligomerization of one embodiment, aluminoxane may preferably be used, and more preferably, methyl aluminoxane (MAO) or modified methyl aluminoxane (MMAO) may be used.

The catalyst system for olefin oligomerization may have a molar ratio of the compound represented by Chemical Formula 1 or 2:a source of transition metal:a cocatalyst of about 0.1:1:1 to about 10:1:10,000, preferably about 0.5:1:100 to about 5:1:3,000, so as to increase selectivity for linear alpha-olefins, especially 1-hexene and 1-octene, and to improve reaction activity. However, the present invention is not limited thereto.

In the catalyst system comprising the compound represented by Chemical Formula 1 or 2, a source of transition metal, and a cocatalyst, the three components of the catalyst system can be added simultaneously or sequentially in a random order in any suitable solvent in the presence or absence of monomers, and thereby be obtained as a catalyst having activity. Suitable solvents include heptane, toluene, cyclohexane, methylcyclohexane, 1-hexene, diethyl ether, tetrahydrofuran, acetonitrile, dichloromethane, chloroform, chlorobenzene, methanol, acetone, etc., but are not limited thereto.

Meanwhile, according to another embodiment of the present invention, there may be provided a method for preparing an olefin oligomer, comprising multimimerizing olefins in the presence of the catalyst system for olefin oligomerization. If the catalyst system for olefin oligomerization according to one embodiment of the invention is used, a method for oligomerizing olefins with improved activity and selectivity may be provided. In this case, the olefin is $C_{2-10}$ alkene, preferably $C_{2-10}$ alpha-olefin, and most preferably ethylene.

The olefin oligomerization according to the present invention may be conducted as a homogeneous liquid phase reaction, a slurry reaction wherein a catalyst system is not dissolved in part or in whole, a two-phase liquid/liquid reaction, or a bulk phase reaction or a gas phase reaction wherein a product olefin acts as a main medium, in the absence or presence of an inert solvent, using the catalyst system for olefin oligomerization and a common device and contact technology, and the homogeneous liquid phase reaction is preferable.

The olefin oligomerization reaction can be carried out in any inert solvent that does not react with a catalyst compound and an activator. Suitable inert solvents include benzene, toluene, xylene, cumene, heptane, cyclohexane, methylcyclohexane, methylcyclopentane, hexane, pentane, butane, isobutane, etc., but are not limited thereto. In this case, the solvent can be used by treating with a small amount of alkylaluminum and thereby removing a small amount of water or air acting as a catalyst poison.

The olefin oligomerization reaction may be carried out at a temperature of about 5° C. to about 200° C., preferably at a temperature of about 30° C. to about 150° C. Further, the olefin oligomerization reaction may be carried out at a pressure from about 1 bar to about 300 bar, preferably at a pressure from about 2 bar to about 150 bar.

According to one embodiment of the present invention, it was confirmed that as a result of oligomerizing ethylene with a catalyst system using the compound represented by Chemical Formula 1 or 2 as a ligand, the catalytic activity and the selectivity of 1-hexene and 1-octene are high.

Advantageous Effects

A catalyst system comprising the compound according to the present invention can oligomerize ethylene with higher catalytic activity and selectivity than existing catalyst systems.

DETAILED DESCRIPTION OF THE EMBODIMENTS

Hereinafter, preferred examples are presented to aid in understanding of the present invention. However, these examples are only for illustrative purposes, and the scope of the present invention is not limited thereto.

Example 1

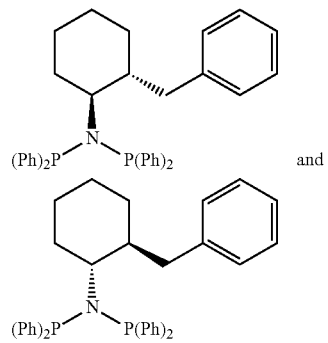

Under argon, 2-benzylcyclohexaneamine (10 mmol) and triethylamine (2-10 equivalents to 2-benzylcyclohexaneamine) were dissolved in dichloromethane (80 mL). While the flask was immersed in a water bath, chlorodiphenylphosphine (1.5-2.0 equivalents to 2-benzylcyclohexaneamine) was slowly added thereto, and the mixture was stirred overnight. After removing the solvent by vacuum drying, THF was added, and the mixture was stirred sufficiently to remove a triethylammnoium chloride salt with an air-free glass filter. After drying the solvent from the filtrate, acetonitrile was added and sufficiently stirred to obtain a ligand compound as a white solid with an air-free glass filter. In this process, compounds other than the ligand compound were dissolved in acetonitrile and separated into a filtrate $^1$H NMR (500 MHz, CDCl$_3$): 7.92-6.93 (25, m), 3.21 (2H, m), 2.77 (1H, m), 1.98 (1H, m), 1.79 (2H, m), 1.54 (3H, m), 1.35 (2H, m), 1.15 (1H, m)

$^{31}$P NMR (202 MHz, CDCl$_3$): 56.5 (s), 54.9 (s)

Example 2

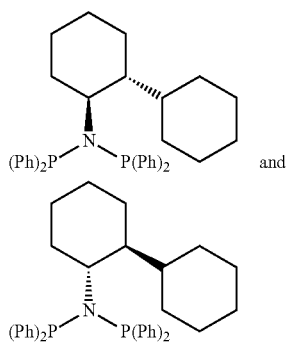

A white solid was obtained in the same manner as in Example except that [1,1'-bi(cyclohexane)]-2-amine was used instead of 2-benzylcyclohexanamine.

$^{31}$P NMR (202 MHz, CDCl$_3$): 53.9 (s), 49.6 (s)

Example 3

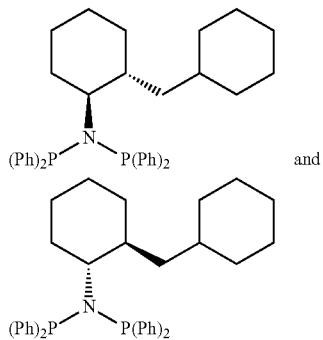

A white solid was obtained in the same manner as in Example 1, except that 2-(cyclohexylmethyl)cyclohexaneamine was used instead of 2-benzylcyclohexanamine.

$^{31}$P NMR (202 MHz, CDCl$_3$): 52.9 (s), 48.4 (s)

Example 4

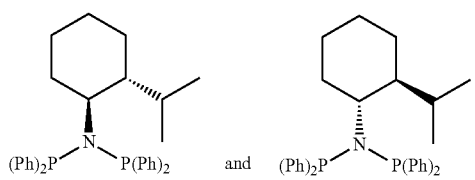

A white solid was obtained in the same manner as in Example 1, except that 2-isopropylcyclohexaneamine was used instead of 2-benzylcyclohexanamine.

$^{31}$P NMR (202 MHz, CDCl$_3$): 62.0 (s), 51.3 (s)

Example 5

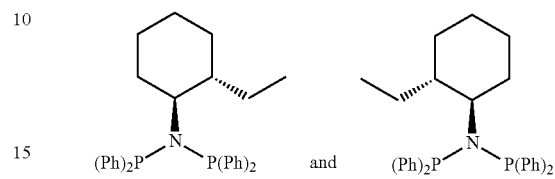

A white solid was obtained in the same manner as in Example 1, except that 2-ethylcyclohexaneamine was used instead of 2-benzylcyclohexanamine.

$^{31}$P NMR (202 MHz, CDCl$_3$): 49.3 (s), 46.7 (s)

Comparative Example

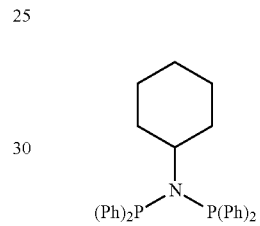

A white solid was obtained in the same manner as in Example 1, except that cyclohexaneamine was used instead of 2-benzylcyclohexanamine. The procedure for separating the remaining compounds other than the ligand compound by adding acetonitrile was omitted.

$^{31}$P NMR (202 MHz, CDCl$_3$): 49.5 (s)

Experimental Example (Step 1)

Under an argon gas, Cr(acac)$_3$ (17.5 mg, 0.05 mmol) and the compounds prepared in Examples and Comparative Example (0.055 mmol) were added to a flask, and 100 mL of methylcyclohexane was added, and the mixture was stirred to prepare a 0.5 mM solution.

(Step 2)

A Parr reactor with a capacity of 600 mL was prepared and vacuumed at 120° C. for 2 hours, then the temperature was lowered to 60° C., and the inside was replaced with argon. Thereafter, 130 g of methylcyclohexane was injected into the Parr reactor, and then a sufficient amount of cocatalyst MMAO (Al/Cr=600-1200) was injected into the Parr reactor, to which 5 mL (2.5 μmop or 2.5 mL (1.25 μmol) of the 0.5 mM solution prepared in the step 1 was injected.

A valve of an ethylene line adjusted to 60 bar was opened to fill the inside of the reactor with ethylene, and then adjusted to preheat to 60° C., and the mixture was stirred at 1000 rpm for 15 minutes. The ethylene line valve was closed, the reactor was cooled to 0° C. with a dry ice/acetone bath, non-reacted ethylene was slowly vented, and then 1 mL of nonane (GC internal standard) was added. After stirring for 10 seconds, 2 mL of the liquid portion of the reactor was taken and quenched with water, and the organic layer was filtered with a PTFE syringer filter to perform GC analysis for the distribution of the liquid product. Ethanol/HCl (10 vol %) was added to the remaining reaction solution, and the mixture was stirred and filtered to obtain a polymer. The obtained polymer was dried overnight in a vacuum oven at 60° C.

(Analysis Results)

The catalytic activity and the components of the product were analyzed by using GC, and the results are shown in Table 1 below. Using the total weight of the product, the catalytic activity was analyzed by dividing the number of moles of Cr and the time of oligomerization reaction. In the product, the content of 1-hexene and 1-octene was determined by HAO, the content of $C_6$-isomer other than 1-hexene by C-iso, and the content of $C_8$-isomer other than 1-octene by C8-iso.

TABLE 1

| | Comparative Example | Example 1 | Example 2 | Example 3 | Example 4 | Example 5 |
|---|---|---|---|---|---|---|
| Catalytic activity (ton/molCr/hr) | 145 | 107 | 444 | 318 | 318 | 376 |
| HAO (wt %) | 87.6 | 90.8 | 91.5 | 91.3 | 91.8 | 90.3 |
| C6-iso (wt %) | 3.4 | 2.2 | 1.4 | 2.0 | 0.9 | 1.8 |
| C8-iso (wt %) | 0.4 | 0.3 | 0.2 | 0.2 | 0.2 | 0.3 |

As shown in Table 1 above, it was confirmed that in the case of Examples, the content of HAO was significantly high and the content of C6-iso was low, as compared with Comparative Example. Further, it was confirmed that all the remaining Examples excluding Example 1 exhibited excellent catalytic activity as compared with Comparative example. Therefore, it was confirmed that the compounds according to the present invention can be usefully used as ligands in the catalyst system for olefin oligomerization.

The invention claimed is:

1. A compound represented by Chemical Formula 1 or 2 below:

[Chemical Formula 1]

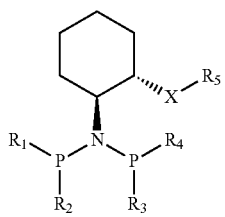

[Chemical Formula 2]

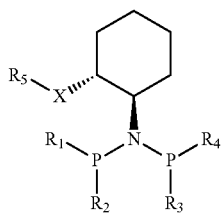

in Chemical Formulas 1 and 2, $R_1$ to $R_4$ are each independently $C_{1-10}$ alkyl; $C_{3-6}$ cycloalkyl unsubstituted or substituted by $C_{1-10}$ alkyl or $C_{1-10}$ alkoxy; $C_{6-20}$ aryl unsubstituted or substituted by $C_{1-10}$ alkyl or $C_{1-10}$ alkoxy; Or $C_{5-20}$ heteroaryl unsubstituted or substituted by $C_{1-10}$ alkyl or $C_{1-10}$ alkoxy, $R_5$ is $C_{3-6}$ cycloalkyl unsubstituted or substituted by $C_{1-10}$ alkyl or $C_{1-10}$ alkoxy; $C_{6-20}$ aryl unsubstituted or substituted by $C_{1-10}$ alkyl or $C_{1-10}$ alkoxy; or $C_{5-20}$ heteroaryl unsubstituted or substituted by $C_{1-10}$ alkyl or $C_{1-10}$ alkoxy, and X is a bond or $C_{1-5}$ alkylene.

2. The compound of claim 1, wherein
$R_1$ to $R_4$ are identical to one another.

3. The compound of claim 1, wherein
$R_1$ to $R_4$ are phenyl.

4. The compound of claim 1, wherein
$R_5$ is cyclopropyl, cyclobutyl, cyclopentyl, cyclohexyl, cyclohexyl substituted with methyl, or phenyl.

5. The compound of claim 1, wherein
X is a bond or methylene.

6. The compound of claim 1, wherein
$R_5$ is $C_{3-6}$ cycloalkyl, or $C_{6-20}$ aryl, and
X is methylene.

7. The compound of claim 1, wherein
$R_5$ is $C_{3-6}$ cycloalkyl, and
X is a bond.

8. The compound of claim 1, wherein
the compound represented by Chemical Formula 1 or 2 is any one selected from the group consisting of the following compounds:

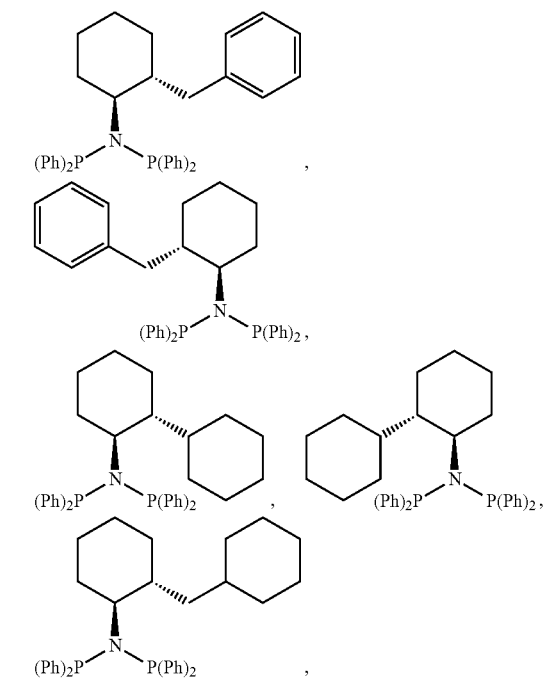

-continued
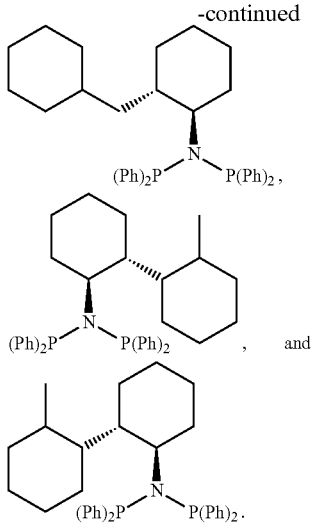
9. A catalyst system for olefin oligomerization, comprising: the compound of claim 1, a source of transition metal, and a cocatalyst.
10. A method for oligomerizing olefins, comprising multimerizing olefins in the presence of the catalyst system for olefin oligomerization of claim 9.
* * * * *